United States Patent [19]

Dyer et al.

[11] Patent Number: 4,695,500
[45] Date of Patent: Sep. 22, 1987

[54] STABILIZED FABRIC

[75] Inventors: John Dyer, Randolph; John W. Kennette, Somerville, both of N.J.

[73] Assignee: Johnson & Johnson Products, Inc., New Brunswick, N.J.

[21] Appl. No.: 884,152

[22] Filed: Jul. 10, 1986

[51] Int. Cl.⁴ .......................... A61F 13/00; B32B 3/10
[52] U.S. Cl. ..................................... 428/134; 28/104; 28/105; 28/106; 128/156; 428/179; 428/187; 428/196; 428/197; 428/219; 428/253; 428/299; 428/303; 428/306.6; 428/317.9; 604/374; 604/377
[58] Field of Search .......................... 28/104, 105, 106; 128/156; 428/134, 179, 187, 196, 197, 219, 253, 255, 299, 303; 604/374, 377

[56] References Cited

U.S. PATENT DOCUMENTS

| | | |
|---|---|---|
| 3,068,547 | 12/1962 | L'Hommedieu . |
| 3,081,515 | 3/1963 | Griswold et al. . |
| 3,129,466 | 4/1964 | L'Hommedieu . |
| 3,485,706 | 12/1969 | Evans . |
| 3,679,535 | 7/1972 | Kalwaites . |
| 4,016,319 | 4/1977 | Marshall . |
| 4,095,007 | 6/1978 | Marshall . |
| 4,379,799 | 1/1983 | Holmes et al. . |
| 4,465,726 | 8/1984 | Holmes et al. . |
| 4,612,226 | 9/1986 | Kennette et al. . |

Primary Examiner—James C. Cannon
Attorney, Agent, or Firm—Wayne R. Eberhardt

[57] ABSTRACT

A loosely constructed knit or woven fabric is dimensionally stabilized by causing staple length textile fibers to be entangled about the intersections of the yarns comprising the fabric. The stabilized fabric is formed by covering one or both sides of the loosely constructed base fabric with a light web of the staple length fibers, and subjecting the composite material to hydraulic entanglement while supported on a porous forming belt configured to direct and concentrate the staple length fibers at the intersections of the yarns comprising the base fabric.

32 Claims, 6 Drawing Figures

FIG-1
FIG-2
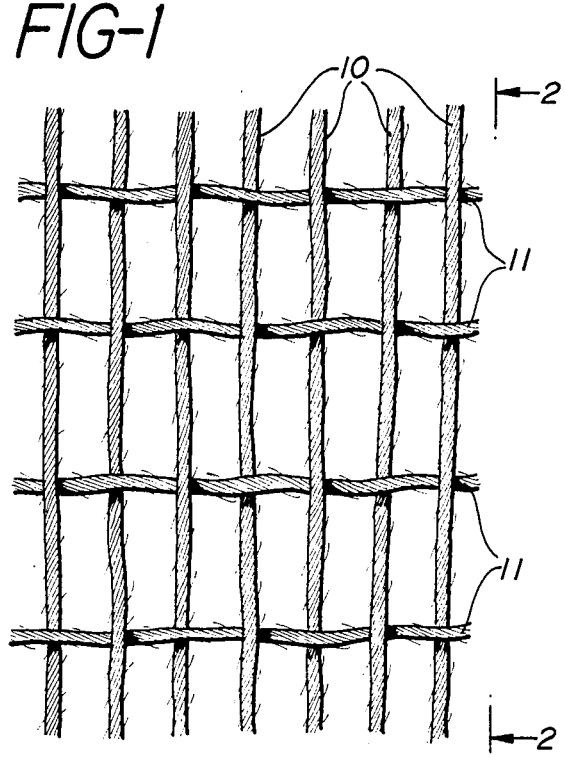
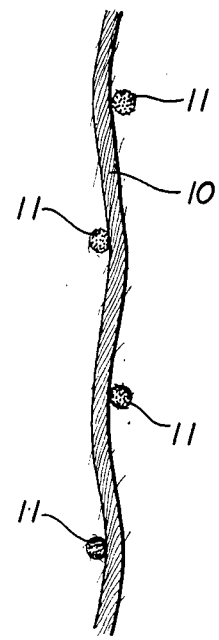
FIG-3
FIG-4
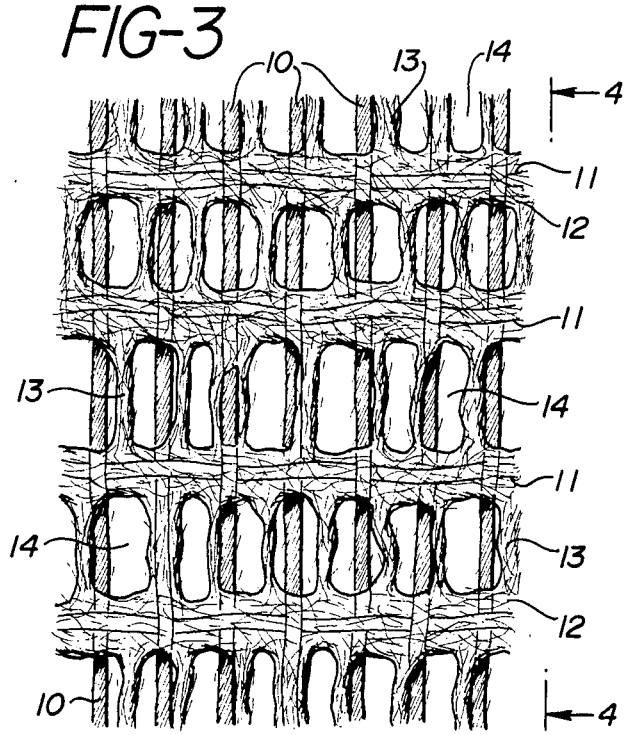
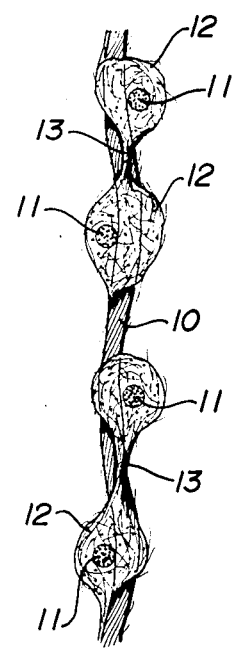

STABILIZED FABRIC

FIELD OF THE INVENTION

This invention relates to a novel fabric construction, and more particularly to a textile material comprising a loosely constructed fabric of spaced apart yarns wherein intersecting yarns are anchored by discontinuous fibers entangled about the yarns at the intersections thereof. A woven gauze fabric stabilized with rayon staple fibers is particularly well suited for use as a surgical sponge.

BACKGROUND OF THE INVENTION

Woven gauze has long been accepted as the standard material for constructing surgical sponges, swabs, dressings, bandages and similar products. The arrangement of yarns in the woven fabric provides a lightweight open structure which is folded to form multi-ply pads. Cotton fiber is used almost exclusively to make the yarn and confers characteristic properties such as absorbency and strength to the fabric. As a consequence of these properties, woven gauze is a versatile fabric used for many different purposes. Gauze sponges and swabs are used to absorb fluid, scrub and clean surfaces, remove dead cells and necrotic tissue (debride), separate tissues and organs (blunt dissection), pack and wall-off cavities, cover and protect organs and tissues during surgery and dress wounds. Gauze may be impregnated with various agents such as betadine (prepping) or petrolatum (dressing) for special applications.

The wet strength of gauze is important when the fabric is used in surgery for holding, lifting and moving organs and even skeletal structures. The low resilience of woven gauze permits the sponges to be packed in cavities or formed into shapes such as points for use in delicate surgery, and assures that the sponges will stay in place as positioned by the surgeon or nurse.

Despite its versatility and application in so many different procedures, there are several undesirable characteristics of conventional woven gauze that can have serious consequences during the use of the fabric in surgery. One such characteristic of gauze fabric is the tendency to shed lint particles. Gauze consists of a loose array of parallel warp yarns interwoven with fill yarns perpendicular to the warp direction. Yarn and fiber fragments are formed during the various operations of slitting, cutting and converting the fabric. Any particles remaining in the finished end product can easily separate from the fabric and contaminate wound and surgical sites.

There is no practical way for cutting gauze in either the warp or fill direction to completely avoid damaging yarns adjacent to the cut. Yarn fragments and even full lengths of yarn close to the cut can easily separate from the structure when the material is used. For this reason, gauze sponges are usually folded so that the cut edges are in the center and remain covered by fabric when the sponge is opened for use. If the user unfolds the sponge and exposes the cut edges, the incidence of linting is significantly increased.

The cotton fiber used to make the yarn is another source of lint. Not only does the initial cotton fiber length vary, but individual fibers are broken as the fiber is carded or combed and twisted together to form the yarn. In the yarn, the fibers are held together only by surface interaction and cohesive forces and many fiber ends protrude from the yarn. Since individual fibers are not firmly secured in the yarn and the yarn may be further degraded during subsequent processing (bleaching, scouring and drying), short fibers and fiber fragments may separate from the individual yarns during use.

Another deficiency of conventional woven gauze is the lack of physical and dimensional stability. When the fabric is worked either dry or wet as by folding, rolling, packing, wringing or pulling, the yarns are able to move independently of one another. Under stress, the yarns move and one displaced do not return to their original position after the stresses have been relaxed. Gauze has very poor burst properties because the yarns move and separate to form a hole in the fabric before they break. Thus the structure of woven gauze is easily deformed and disrupted by the stresses encountered in use. At extremes of stress during use, the integrity of the fabric can be completely destroyed with yarn and fiber fragments separating from the structure.

Griswold, U.S. Pat. No. 2,860,068, has shown that loosely woven structures such as gauze can be stabilized by applying a binder to the fabric in such a way that at least 20% of the warp and fill yarn intersections are bonded together. Gauze stabilized in this way was used as a facing fabric for sanitary napkins. However, the binder adversely affects absorbency and causes the fabric to become stiff, especially at higher levels of application where up to 50% of the yarn intersections may be bonded together, rendering such bonded gauze less desirable for use in sponges and other surgical products.

It is accordingly an object of the present invention to provide an improved woven gauze fabric for use in surgical applications. It is a further object to provide a gauze fabric having improved dimensional stability, integrity and handling properties. Another object of the present invention is to provide a gauze fabric having improved fluid absorption properties. A further object of the invention is to provide a novel stabilized fabric comprising a loosely constructed fabric of spaced apart yarns wherein intersecting yarns are anchored by staple fibers entangled about the yarns at the intersections thereof, and a method for preparing such stabilized fabric.

SUMMARY OF THE INVENTION

The novel fabrics of the present invention comprise a loosely constructed base fabric such as a woven fabric wherein spaced apart warp and fill yarns are dimensionally stabilized by staple fibers which are physically entangled about the yarns at the intersections thereof. The staple fibers anchor all or most of the yarn intersections in the fabric without completely encasing the base fabric structure so that the stabilized material retains the original identity of the base fabric. The base fabric is suitably woven surgical gauze, and the additional staple fibers are suitably cotton or rayon staple.

The stabilized fabrics of the present invention may be formed using hydraulic entanglement procedures wherein, for example, a gauze fabric is covered on one or both sides with a light web of staple fibers and subjected to high pressure liquid jets while supported on a liquid pervious forming belt. Such methods of hydraulic entanglement are known in the art for the preparation of nonwoven fabrics from staple fibers as described for example in L'Hommedieu, U.S. Pat. No. 3,129,466; Evans, U.S. Pat. No. 3,485,706; and Holmes U.S. Pat. Nos. 4,379,799 and 4,465,726.

The stabilized fabrics of the present invention retain the general appearance and many of the desirable physical characteristics of the base fabric. Substantial portions of the yarns of the base fabric remain completely exposed while others may be almost totally encased by staple fiber providing discrete and functionally different zones in the fabric. Surgical gauze stabilized in accordance with the present invention retains the ability of gauze to scrub and debride wounds while having improved softness, increased liquid absorption capacity and substantially lint-free properties as compared to plain gauze fabric.

DESCRIPTION OF DRAWINGS

FIG. 1 is an enlarged diagramatic plan view of conventional open weave, unbonded surgical gauze.

FIG. 2 is an edge view of the fabric of FIG. 1 taken on line 2—2.

FIG. 3 is an enlarged, diagramatic plan view of a stabilized gauze fabric in accordance with the present invention.

FIG. 4 is an edge view of the fabric of FIG. 3 taken on line 4—4.

DESCRIPTION OF PREFERRED EMBODIMENTS

Figure 5:
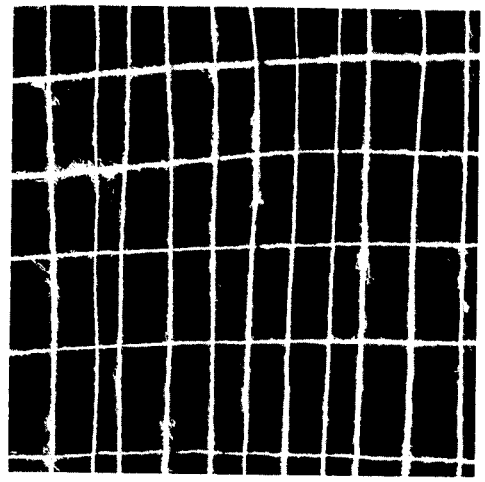
FIG. 5 is a photograph at approximately 5X enlargement of conventional surgical gauze having 14×8 yarns per inch.

The stabilized fabrics of the present invention are hereinafter described with particular reference to fabrics based on woven absorbent gauze stabilized with rayon stable fibers which are particularly well suited for use in surgical and wound care applications. It will be understood that the method of the present invention can be used to prepare novel stabilized woven or knit fabrics of other constructions and such fabrics are also included within the scope of the present invention.

FIG. 1 illustrates a typical woven gauze fabric having an open structure comprising warp yarns 10 extending in the machine direction and fill yarns 11 crossing at right angles to the warp yarns. The yarns are not secured at the intersection and consequently are easily displaced by external forces. Yarns running near the cut edge of the fabric are readily separated from the fabric. In cross section, as illustrated in FIG. 2, the fabric is thin and a single ply has little bulk.

FIG. 3 illustrates a stabilized gauze in accordance with the present invention comprising the woven gauze fabric of FIG. 1 wherein the individual yarns are partially covered in defined areas by fibers 12. In the illustrated embodiment, the fill yarns 11 are substantially encased over their entire length by the entangled staple fibers, while the warp yarns 10 are largely uncovered except at the areas of intersection with the fill yarns.

Referring further to FIG. 3, the entangled staple fiber component of the composite fabric includes fibrous bundles 13 extending in the warp direction between encased fill yarns. Fibrous bundles 13 are substantially parallel to the warp yarns of the woven gauze component of the fabric, but are preferably not in registry with the warp yarns. While fibrous bundles 13 may occasionally overlap or encase a warp yarn, at least a major portion of the warp yarns are preferably left substantially uncovered when the stabilized fabric is intended for use as surgical gauze.

The stabilized gauze of the present invention has increased single-ply bulk compared to plain woven gauze. As illustrated in FIG. 4, the increased bulk is concentrated in the area of the fill yarns which are substantially encased by the staple fibers. Fibrous bundles 13 extending between fill yarns in the warp direction add little to the bulk of the fabric, but contribute substantially to other physical properties such as softness and absorbency.

The fibrous bundles 13 of the stabilized fabric define a plurality of openings 14 between adjacent fibrous bundles. The size and spacing of these openings is determined by the topography of the liquid pervious forming belt used to support the fabric during hydraulic entanglement. While openings 14 could be controlled to coincide with the openings in the woven gauze fabric, the majority of fibrous bundles 13 preferably do not coincide with the warp yarns. Most preferably, at least 50 percent of the warp yarns are left substantially bare of stabilizing fibers except at intersections with fill yarns, thereby imparting to the stabilized fabric many of the more desirable attributes of the woven gauze base fabric.

Figure 6:
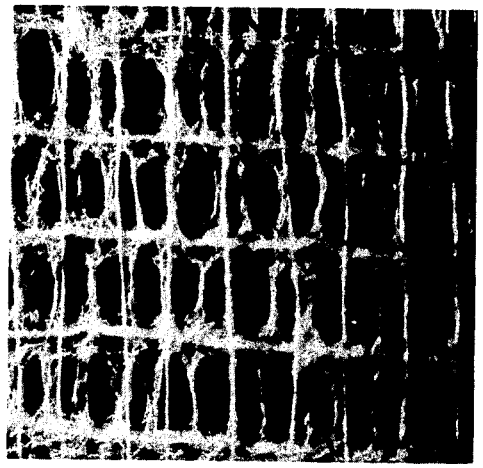
FIG. 6 is a photograph at approximately 5X enlargement of the surgical gauze of FIG. 5 stabilized in accordance with the present invention.

FIG. 5 is a 5X photoenlargement of conventional surgical gauze having 14×8 yarns per inch. FIG. 6 is a 5X photoenlargement of a stabilized gauze fabric produced in accordance with the present invention and comprising the surgical gauze of FIG. 5 stabilized with approximately 68 percent by weight added rayon staple fibers.

In the stabilized fabric of FIG. 6 wherein a substantial number of the warp yarns remain uncovered by the staple fibers, the surface of the fabric includes two distinct and functionally different structures. The fiber encased fill yarns add structural stability and absorbency to the fabric, and cause the fabric to function as a soft, cushioning swab when used in a wiping motion perpendicular to the fill yarns. The substantially uncovered warp yarns retain their original characteristics and cause the fabric to function as a coarser, scrubbing or debriding sponge when used in a wiping motion perpendicular to the warp yarns.

In an alternative embodiment, the staple fibers are concentrated specifically in the areas of the intersecting warp and fill yarns so that substantial portions of both warp and fill yarns remain uncovered. Such a stabilized fabric is obtained by the use of an appropriately configured forming belt which causes the loose staple fibers to wash into the desired areas during hydraulic entanglement. A suitable belt is one characterized by having a plurality of spaced apart surface depressions in registry with the intersections of the yarns comprising the base fabric. The stabilized fabric is characterized by improved softness and absorbent properties as well as improved dimensional stability with little increase in bulkiness.

A typical woven surgical gauze may have from 10 to 20 yarns per inch in the warp or machine direction and 6 to 12 yarns per inch in the cross or fill direction, and may have a basis weight of from 0.10 to 2.0 oz/yd$^2$ (3.4–67.8 g/m$^2$). A representative surgical gauze of 14×8 yarns per inch has an average basis weight of about 0.40 oz/yd$^2$ (13.6 g/m$^2$), while 20×8 gauze has an average basis weight of about 0.60 oz/yd$^2$ (20.3 g/m$^2$). Basis weight for gauze samples was determined by weighing an accurately measured piece of the fabric after conditioning at 65 percent relative humidity for at least four hours. Stabilized gauze fabrics were prepared by placing lightweight webs of staple fiber on one or both sides of the woven gauze and subjecting the stabilized material to hydraulic entanglement. The staple fiber may have a denier of from about 1.0 to 3.0 and a staple length of from about 0.5 to 2.0 inches, and may constitute from about 10 to 70 percent by weight of the stabilized fabric. In the following examples, the staple fiber was 1.5 denier, 1.25 inch rayon staple, and staple fiber webs weighing from 0.10 to 0.40 oz/yd$^2$ (3.4–13.6 g/m$^2$) were applied to both sides of the woven gauze prior to entanglement.

The method and apparatus used to prepare the stabilized gauze of the following examples was substantially as disclosed in Holmes, U.S. Pat. Nos. 4,379,799 and 4,465,725 for producing a nonwoven fabric by hydraulic entanglement on a porous forming belt, which disclosures are incorporated herein by reference. The forming belt of Holmes is characterized by a topography of alternating parallel ridges and valleys across the width of the belt as illustrated, for example, in FIGS. 6 and 7 of the U.S. Pat. No. 4,465,726. In the method of the present invention, the spacing of the valleys on the surface of the forming belt corresponds substantially to the spacing of the fill yarns in the woven fabric so that, during the process of hydraulic entanglement, the fill yarns are washed into the valleys where they are substantially encased with staple fibers which are also washed into the valleys. The warp yarns of the surgical gauze which pass over the ridges of the forming belt are left relatively free of staple fibers.

EXAMPLES

Standard surgical gauze having 14×8 yarns per inch was processed with rayon staple fibers to produce four stabilized gauze fabrics wherein the rayon staple accounted for approximately 25, 40, 50 and 70 percent by weight of the stabilized fabric. The stabilized fabrics were tested for physical properties with the results presented below.

1. Tear Strength:

The average force required to continue a tongue type tear in each fabric through a fixed distance was determined using an Elmdorf Tearing gauge. The fabrics were preconditioned for at least four hours at 50 percent relative humidity and cut accurately in each principal direction of the fabric to obtain samples 7.6 cm long by 6.3 cm wide. A slit 20 mm long was cut from the center edge of the sample length leaving exactly 43 mm from the end of the slit to the opposite edge of the specimen. A 1600 g. pendulum was used to complete the tear.

TABLE I

| | Avg. Tear Strength (g) | |
|---|---|---|
| Wt. % Gauze | Warp | Fill |
| 100 | — | — |
| 75 | 743 | 915 |
| 61 | 781 | 998 |
| 51 | 733 | 1318 |
| 32 | 776 | 1106 |

Meaningful tear strength values could not be obtained for 100% gauze since the loosely woven material disintegrated before tearing by yarns pulling free from the structure. As little as 25 wt% added rayon staple fiber, however, was sufficient to stabilize the gauze structure so that it could be torn by this test.

2. Tensile Strength:

A continually increasing load was applied longitudinally to a 4×6 inch fabric sample using an Instron Tensile Tester. The sample was held by clamps 1 inch wide and spaced 3 inches apart at the start of the test. After mounting, the fabric was carefully cut from the edges to the sides of the clamps so that the material was supported only by the one inch of fabric held by the clamps. Breaks were made in the machine direction, cross direction, and on the bias. The rate of clamp separation was 12 inches/minute. Values for extension at break were calculated as percentage of starting length (3 inches).

TABLE II

| | | Avg. Tensile Strength (lbs.)/Extension (%) | | | | |
|---|---|---|---|---|---|---|
| Wt. % Gauze | Basis Wt. Oz/yd$^2$ | Warp | | Fill | | Bias | |
| | | lbs. | % | lbs. | % | lbs. | % |
| 100 | .41 | 8.02 | 5.9 | 3.58 | 8.9 | .24 | 54.4 |
| 64.5 | .63 | 6.84 | 6.7 | 2.40 | 12.8 | 4.47 | 55.2 |
| 62.3 | .66 | 8.90 | 8.7 | 2.62 | 12.3 | 4.31 | 52.0 |
| 57.3 | .71 | 7.81 | 7.0 | 2.97 | 11.8 | 5.42 | 46.0 |
| 48.7 | .84 | 7.92 | 7.3 | 2.40 | 13.0 | 5.31 | 54.7 |
| 47.7 | .86 | 8.19 | 7.7 | 4.46 | 14.3 | 6.65 | 45.4 |
| 42.2 | .97 | 7.43 | 6.7 | 1.82 | 12.7 | 6.43 | 53.3 |
| 33.9 | 1.20 | 10.60 | 8.7 | 3.60 | 20.3 | 7.08 | 48.7 |
| 31.2 | 1.31 | 10.00 | 9.0 | 3.46 | 33.3 | 5.97 | 60.0 |
| 0 | .73 | 2.67 | 26.3 | 2.22 | 43.8 | 2.37 | 38.6 |
| 0 | 1.00 | 4.32 | 18.0 | 2.03 | 72.3 | 2.44 | 56.0 |
| 0 | 1.18 | 5.32 | 17.3 | 3.42 | 48.0 | 3.27 | 39.0 |

In the Tensile Strength Test, plain gauze breaks with complete disruption of the fabric structure, that is, the yarns break at various locations so that the integrity of the fabric is destroyed. The stabilized gauze on the other hand, breaks in a more uniform manner across the width of the fabric and pieces remaining after the break retain most of their original structure. On the bias, plain gauze has virtually no strength since the yarns simply pull free rather than break. Stabilized gauze has excellent strength on the bias. As compared to gauze-free rayon staple fabric, stabilized gauze has more than twice the bias strength.

3. Burst Strength:

Dry and wet test samples at least 2.5×2.5 inches were mounted over a 1.2 inch diameter diaphragm and held rigidly at the circumference. The bursting strength was determined as the hydrostatic pressure in lb/sq.in. required to rupture the material when pressure was applied through the diaphragm at an increasing rate of 1.8 psi/min. The apparatus used was a Mullen burst tester manufactured by B. F. Perkins and Son, Holyoke, Mass.

TABLE III

| | Avg. Burst Strength | |
|---|---|---|
| Wt. % Gauze | Burst Strength (psi) | |
| | Dry | Wet |
| 100 | 10.6 | 12.8 |
| 73 | 10.6 | 12.7 |
| 57 | 9.9 | 13.8 |
| 50 | 10.9 | 15.0 |
| 32 | 15.4 | 15.7 |

Plain gauze has very poor burst properties because the yarns move and separate to form a hole in the fabric before they break. As indicated by the above data, the burst strength of the stabilized gauze as determined by this test is not appreciably improved by the addition of up to 50 wt% rayon fibers, although significant improvement is observed at 32% gauze/68% rayon fibers. In the Mullen burst test, the fabric is mounted in such a way that the stabilizing effect of the added rayon staple fiber is not evident. In actual use however, where the gauze is placed over the tip of a finger, the yarns in the stabilized fabric are not easily separated and the fabric is resistant to forming a hole.

4. Absorbent Capacity:

A weighed folded sponge was dropped onto the surface of water contained in a tray. After ten seconds the submerged sample was carefully removed using a forceps to hold one corner and allowed to drip for one minute. The wet weight of the sponge was then measured and the amount of fluid absorbed calculated. The absorbent capacity was expressed as grams of fluid per gram dry sponge weight.

A fabric produced exclusively of rayon staple fibers by simply omitting the gauze from the assembly presented for hydraulic entanglement had a measured absorptive capacity of 9.58 g/g. The absorptive capacity of plain gauze was determined to be 5.0 g/g. These values were used to predict the absorptive capacity of the stabilized gauze samples on the basis of staple fiber content. The excess of measured capacity over predicted capacity was calculated and reported in Table IV as Enhanced Capacity.

TABLE IV

| Wt. % Gauze | Absorbent Capacity | | |
|---|---|---|---|
| | Measured Capacity (g/g) | Predicted Capacity (g/g) | Enhanced Capacity (%) |
| 100 | 5.00 | — | — |
| 65 | 8.78 | 6.60 | 133 |
| 52 | 9.05 | 7.19 | 126 |
| 45 | 9.49 | 7.52 | 126 |
| 31 | 8.95 | 8.16 | 110 |
| 0 | 9.58 | — | — |

The ability of a surgical sponge to absorb fluid rapidly and the total absorbent capacity determine the effectiveness of a sponge in maintaining a clean, dry operating site during surgery. The loose open structure of woven gauze allows fluid to pass rapidly into a sponge pad, but the absorbent capacity of the fabric is low. When the woven gauze is stabilized by adding rayon staple fiber, a substantial improvement in the absorbent capacity is achieved. The observed absorbent capacity of the stabilized gauze sponge in these examples is unexpectedly 10–33% greater than would be predicted from the individual capacities of the plain gauze and rayon stable fabric.

The absorbent capacity of various sponges made from plain and stabilized gauze and having from 4 to 16 plies is given in Table V and VI. As a consequence of the enhanced absorbency of the stabilized gauze, less material is needed to absorb equal or greater amounts of liquid as compared to plain gauze. Thus, the absorbent capacity of four plies of stabilized gauze comprising 69% rayon staple fibers or 8 plies comprising 35% rayon staple fibers is more than equivalent to the capacity of a conventional 16 ply plain gauze sponge. On a unit weight basis, the stabilized gauze has a 40 to 50 percent advantage in total absorptive capacity over plain gauze.

TABLE V

| | | Absorbent Capacity (g. water absorbed) 4 × 4 Sponges | | | | | | |
|---|---|---|---|---|---|---|---|---|
| Wt. % Gauze | Basis Wt. oz/yd² | Number of Plies | | | | Avg. g/Ply | g/Ply/ Unit Wt. | % Incr. |
| | | 4 | 8 | 12 | 16 | | | |
| 100 | 0.37 | — | — | 10.2 | 13.0 | .83 | 2.2 | — |
| 65 | 0.57 | — | 14.0 | — | — | 1.75 | 3.1 | 41 |
| 52 | 0.71 | 8.8 | 18.0 | — | — | 2.23 | 3.1 | 41 |
| 45 | 0.82 | 11.0 | 21.5 | — | — | 2.71 | 3.3 | 50 |
| 31 | 1.20 | 14.6 | 30.1 | — | — | 3.73 | 3.1 | 41 |

TABLE VI

| | | Absorbent Capacity (g. blood absorbed) 4 × 4 Sponges | | | | | | |
|---|---|---|---|---|---|---|---|---|
| Wt. % Gauze | Basis Wt. oz/yd² | Number of Plies | | | | Avg. g/Ply | g/Ply/ Unit Wt. | % Incr. |
| | | 4 | 8 | 12 | 16 | | | |
| 100(a) | 0.57 | — | 8.4 | 12.3 | 18.6 | 1.1 | 1.9 | — |
| 31(b) | 1.20 | 17.9 | 34.7 | — | — | 4.4 | 3.7 | 95 |

(a) 20 × 8 plain gauze
(b) 14 × 8 stabilized gauze

In addition to the absorbent capacity, the rate of absorption is an important sponge performance characteristic. Common practice is to use the sponge in a dabbing motion to remove fluid from surfaces and rapid absorbence is desired. In a simple qualitative procedure, twenty drops of colored water on a plastic sheet were removed by dabbing each drop with a sponge fabric held firmly in place over the index finger. The same position of the fabric was used for all twenty drops. One ply of stabilized gauze was used for every four plies of plain gauze to provide approximately equivalent total absorptive capacity. A surgeon's glove was worn and the dabbing was smooth, once at each drop, such that all twenty drops were dabbed in about twenty seconds. Immediately after dabbing was complete, fluid remaining on the plastic sheet was blotted onto a paper towel. The extent of staining on the paper towel indicated that the stabilized gauze removed substantially more fluid than the plain gauze in this simple test.

Stabilized gauze is less subject to shedding lint and fiber particles than the plain gauze component of the fabric. Loose surface lint was determined by an adhesive pull-off test wherein a weighed piece of adhesive coated film having an area of 3.75 sq.in. was applied to the surface of the fabric, then peeled off and reweighed to determine weight of fiber pick-up. The results of this test are presented in Table VII.

TABLE VII

| | Surface Lint |
|---|---|
| Wt. % Gauze | Weight of Fiber Pick-Up |
| 100 | 0.86 mg. |
| 34 | 0.26 |

In a further test of fabric integrity and resistance to linting, sponges of plain gauze and stabilized gauze having approximately equivalent total absorptive capacity were subjected to the mechanical action of tumbling in an airstream to dislodge loose fibers and particles. The particulate material from five sponges each tumbled for two minutes was collected and weighed. The sponges were refolded and again tumbled for two minutes after a two-inch cut had been made to the center from the folded edge. Results of the experiment indicated the resistance to mechanical degradation for plain and stabilized gauze sponges as reported in Table VIII.

TABLE VIII

| | | Total Fabric Lint | | |
|---|---|---|---|---|
| Wt. % Gauze | No. of Plys | Initial Fiber Loss mg. | Add'l Fiber Loss with 2" Cut, mg. | Absorbent Capacity (g) |
| 100% | 16 | 75.8 | 108.8 | 11.4 |
| 44% | 4 | 14.1 | 9.7 | — |
| 34 | 4 | 14.7 | 8.8 | 13.9 |

The stabilized gauze fabrics of the present invention are substantially more resistant to shedding than plain surgical gauze. The stabilization of the fabric is such that the material may be cut to any desired shape or size at the time of use without creating the problem of loose fiber fragments characteristic of plain gauze.

The deposition of rayon staple fiber on the gauze fabric as illustrated in FIGS. 3 and 4 produces a ribbed fabric surface. When cut and folded into a multi-ply sponge, the fabric layers nest together, reducing the overall bulk of the sponge without affecting single ply thickness. This effect, in combination with the fact that fewer plys of the fabric of the present invention are required to obtain equivalent absorptive capacity, results in a less bulky, more conformable sponge which is highly desirable for surgical use.

While the present invention has been described principally with reference to stabilized gauze for use as a surgical sponge, the invention is not limited to this specific product or application. The method of the present invention, broadly stated, selectively positions and entangles discontinuous staple length fibers with the intersecting yarns of a loosely woven or knit fabric, and thereby stabilizes the physical structure of the fabric. The method of the present invention may accordingly find application wherever the integrity, handling characteristics, dimensional stability and other physical properties of a loosely constructed fabric or similar arrangement of yarns are desired to be improved. Such applications include open, net-like fabrics for consumer and industrial applications such as clothing, filter screens, wipes, carpet backing, containers, and the like, and particularly woven fabrics containing from 2 to 30 yarns per inch in each direction.

The staple fibers which may be used to stabilize the loosely constructed base fabrics may be rayon, cotton, polyester, polyolefin, acrylic, or other fiber compositions. Webs of such staple fibers may be prepared by carding or otherwise mechanically separating and layering the fibers in a random or oriented manner, or random webs may be formed by air layering. Staple fibers may be from about 0.5 to 4 denier and 0.5 to 3.0 inches in length depending upon the composition of the fiber and the mechanism used for producing the webs prior to hydraulic entanglement. Discontinuous fiber webs suitable for use in the present invention may also be produced directly by melt-blown procedures known in the art.

As will be apparent to those skilled in the art, the stabilized fabrics of the present invention include a large number of loosely constructed fabrics stabilized with discontinuous fibers of various compositions and in various combinations. All such stabilized open fabrics and the method of producing such fabrics as disclosed herein are included within the scope of the present invention.

We claim:

1. A stabilized fabric comprising a loosely woven component and a staple fiber component,
   said woven component comprising a plurality of substantially parallel, spaced apart warp yarns intersecting at right angles with a plurality of substantially parallel spaced apart fill yarns, said warp and fill yarns defining a plurality of openings in said woven component,
   said staple fiber component comprising staple length fibers entangled about said warp and fill yarns without completely encasing said woven component, said staple fibers substantially anchoring said warp and fill yarns at the intersections thereof,
   said stabilized fabric maintaining a plurality of openings defined by said warp and fill yarns.

2. The fabric of claim 1 wherein each of said warp yarns and said fill yarns are spaced to provide from 2 to 30 yarns per inch.

3. The fabric of claim 1 wherein said staple fibers are from 0.5 to 3.0 inches in length.

4. The fabric of claim 1 wherein said staple length fibers comprise from 10 to 70 percent by weight of the stabilized fabric.

5. The fabric of claim 1 wherein said woven component comprises a surgical gauze.

6. The fabric of claim 5 wherein said surgical gauze has from 10 to 20 warp yarns and 6 to 12 fill yarns per inch.

7. The fabric of claim 6 wherein said gauze has a basis weight of from about 0.1 oz/yd to 2.0 oz/yd.

8. The fabric of claim 5 wherein said fibrous component comprises rayon staple fibers having a length of from 0.5 to 2.0 inches.

9. The fabric of claim 8 wherein said fill yarns are substantially totally encased by said staple fibers and said warp yarns are substantially uncovered except where intersecting with said fill yarns.

10. The fabric of claim 1 wherein said woven component comprises surgical gauze having 14×8 yarns per inch, and said fibrous component comprises rayon staple fibers constituting from 10 to 70 percent by weight of the stabilized fabric.

11. The fabric of claim 10 wherein said rayon staple fibers are substantially 1.5 denier and 1.25 inches in length.

12. The fabric of claim 1 wherein said woven component comprises surgical gauze having 20×8 yarns per inch, and said fibrous component comprises rayon staple fibers and constituting from 10 to 70 percent by weight of the stabilized fabric.

13. The fabric of claim 12 wherein said rayon staple fibers are substantially 1.5 denier and 1.25 inches in length.

14. A stabilized surgical gauze comprising a woven fabric component and a staple fiber component,
   said woven component comprising warp and fill yarns and having from 6 to 12 yarns per inch in one direction and from 10 to 20 yarns per inch in the other direction, whereby said intersecting yarns define a plurality of openings in said woven fabric component,
   said staple fiber component comprising staple length fibers, entangled about said yarns at the intersections thereof without completely encasing said fabric, said staple length fibers substantially anchoring said yarns at the intersections thereof, whereby said woven fabric is physically stabilized against relative displacement of said yarns.

15. The surgical gauze of claim 14 wherein the woven component comprises 14×8 yarns per inch, and the staple fiber component comprises from 10 to 70 percent by weight of the stabilized gauze.

16. The surgical gauze of claim 15 wherein said staple fiber component comprises rayon fiber having a staple length of from 0.5 to 2.0 inches and a denier of from 1.0 to 3.0.

17. The surgical gauze of claim 15 wherein a major portion of the yarns extending in one direction are encased by the staple length filaments while a major portion of the yarns extending in the other direction are left substantially uncovered.

18. The surgical gauze of claim 14 wherein the woven component comprises 20×8 yarns per inch, and the staple fiber component comprises from 10 to 70 percent by weight of the stabilized gauze.

19. The surgical gauze of claim 18 wherein said staple fiber component comprises rayon fiber having a staple length of from 0.5 to 2.0 inches and a denier of from 1.0 to 3.0.

20. The surgical gauze of claim 18 wherein a major portion of the yarns extending in one direction are encased by the staple length filaments while a major portion of the yarns extending in the other direction are left substantially uncovered.

21. A method for physically and dimensionally stabilizing a loosely woven fabric composed of spaced apart warp and fill yarns, said method comprising
   a. forming a fibrous web of staple length fibers,
   b. positioning said fibrous web on one or both surfaces of said loosely woven fabric to form a layered structure,
   c. supporting said layered structure on a liquid pervious forming belt having a series of surface ridges and valleys extending in one direction, said valleys being substantially in registry with one of said warp and fill yarns of said woven fabric,
   d. subjecting said layered structure to hydraulic entanglement while supported on said forming belt whereby the staple fibers of said fibrous web are entangled about said warp and fill yarns and substantially anchor said yarns at the intersections thereof, whereby said warp and fill yarns are restrained from movement relative to one another and said fabric is physically and dimensionally stabilized.

22. The method of claim 21 wherein said staple length fibers are from 0.5 to 3.0 inches long and from 0.5 to 4.0 denier.

23. The method of claim 21 wherein said loosely woven fabric has from 2 to 30 yarns per inch in said warp and fill directions.

24. The method of claim 21 wherein said valleys of said forming belt are substantially in registry with the fill yarns of said woven fabric, and said fill yarns are substantially totally encased by said staple fibers as a result of said hydraulic entanglement.

25. A stabilized fabric comprising a loosely constructed base fabric composed of spaced apart intersecting yarns defining a plurality of openings in said base fabric and a discontinuous fiber component comprising a plurality of fibers entangled about said intersecting yarns of said base fabric without completely encasing said yarns, said discontinuous fibers substantially anchoring said intersecting yarns at the intersections thereof, said stabilized fabric including a plurality of openings defined by said intersecting yarns of said base fabric.

26. The fabric of claim 25 wherein said loosely constructed base fabric is a woven fabric comprising a plurality of spaced apart warp yarns intersecting at right angles with a plurality of spaced apart fill yarns.

27. The fabric of claim 25 wherein said loosely constructed base fabric is a knit fabric.

28. The fabric of claim 25 wherein said discontinuous fiber component comprises staple length textile fibers.

29. A method for physically and dimensionally stabilizing a loosely constructed fabric composed of spaced apart intersecting yarns, said method comprising
   a. forming a fibrous web of discontinuous fibers,
   b. positioning said fibrous web on one or both surfaces of said loosely constructed fabric to form a layered structure,
   c. supporting said layered structure on a liquid pervious forming belt having a series of porous surface depressions, said depressions being substantially in registry with the intersections of the yarns of said fabric,
   d. subjecting said layered structure to hydraulic entanglement while supported on said forming belt whereby the discontinuous fibers of said fibrous web are entangled abut said intersecting yarns and substantially anchor said yarns at the intersections thereof, whereby said yarns are restrained from movement relative to one another and said fabric is physically and dimensionally stabilized.

30. The method of claim 29 wherein said discontinuous fibers are staple length fibers from 0.5 to 3.0 inches long and from 0.5 to 4.0 denier.

31. The method of claim 29 wherein said loosely constructed fabric is a woven fabric having from 2 to 30 yarns per inch in the warp and fill directions.

32. The method of claim 29 wherein said loosely constructed fabric is a knit fabric.

* * * * *